(12) United States Patent
Davis

(10) Patent No.: US 8,530,693 B1
(45) Date of Patent: Sep. 10, 2013

(54) LIQUID CYANATE ESTERS

(75) Inventor: Matthew C. Davis, Ridgecrest, CA (US)

(73) Assignee: The United States of America as Represented by the Secretary of the Navy, Washington, DC (US)

( * ) Notice: Subject to any disclaimer, the term of this patent is extended or adjusted under 35 U.S.C. 154(b) by 376 days.

(21) Appl. No.: 12/955,000

(22) Filed: Nov. 29, 2010

(51) Int. Cl.
*C07C 263/12* (2006.01)
(52) U.S. Cl.
USPC ........................................................ 560/346
(58) Field of Classification Search
CPC ................................................... C07C 263/12
See application file for complete search history.

(56) References Cited

U.S. PATENT DOCUMENTS 6,572,980 B1 *  6/2003  Klemarczyk et al. ......... 428/620

* cited by examiner

*Primary Examiner* — Paul A Zucker
(74) *Attorney, Agent, or Firm* — Charlene A. Haley

(57) ABSTRACT

A method for making liquid cyanate esters and liquid cyanate esters. Embodiments of the invention address the problems with solid cyanate esters by creating new cyanate ester structures that are liquid at room temperature. These liquid cyanate esters may be useful for the typical composite fabrication methods including, but not limited to, infusion molding, prepeg consolidation, resin and vacuum transfer molding.

5 Claims, No Drawings

LIQUID CYANATE ESTERS

STATEMENT REGARDING FEDERALLY SPONSORED RESEARCH OR DEVELOPMENT

The invention described herein may be manufactured and used by or for the government of the United States of America for governmental purposes without the payment of any royalties thereon or therefor.

FIELD OF THE INVENTION

The invention generally relates to liquid cyanate esters, and more specifically, liquid cyanate esters with structures that are liquid at room temperature for convenient composite formulation.

DETAILED DESCRIPTION

Embodiments of the invention generally relate to liquid cyanate esters and the methods of making the same.

Embodiments of the invention addresses the problems with solid cyanate esters by creating new cyanate ester structures that are liquid at room temperature. These liquid cyanate esters may be useful for the typical composite fabrication methods including, but not limited to, infusion molding, prepeg consolidation, resin and vacuum transfer molding.

The method for making liquid cyanate ester includes, but is not limited to the following procedures. A benzenecarboxylic acid having from one to six carboxylic acids with an appropriate reagent including thionyl chloride to generate the corresponding benzenecarbonyl chloride. The effective reagent may include, but not limited to, at least one of thionyl chloride and analogous reagents. The benzenecarbonyl chloride is reacted by Friedel-Crafts conditions (aluminum trichloride, and other effective materials) with an alkoxybenzene compound to produce a poly(alkoxybenzoyl)benzene. The alkoxybenzene employed can have one to three alkoxy substituents, including anisole, 1,3,5,-trimethoxybenzene, 1,3,-dimethoxybenzene, or 1,4,-dimethoxybenzene.

The poly(alkoxybenzoyl)benzene is reacted with a Wittig reagent to generate a poly(alkoxyphenylvinyl)benzene compound which is then reduced to a poly(alkoxyphenylalkyl)benzene (reductioning of said poly(alkoxyphenylvinyl)benzene compound with at least one reducing agent (hydrogen, palladium on carbon, and Raney nickel) to produce a poly(alkoxyphenylalkyl)benzene). The poly(alkoxyphenylalkyl)benzene is then reacted with the appropriate reagent (at least one of boron tribromide, pyridine hydrochloride, and aluminum triiodide) to demethylate the methoxy groups to generate a poly(hydroxyphenylalkyl)benzene. The poly(hydroxyphenylalkyl)benzene compound is cyanated by reaction with cyanogen halide (CNBr or CNCl or any combination thereof) and base to give the poly(cyanatophenylalkyl)benzene. Also the liquid cyanate esters, derivatives, isomers and diastereomers that are produced by the methods above are included in the embodiments of the invention.

Chemical Scheme 1.

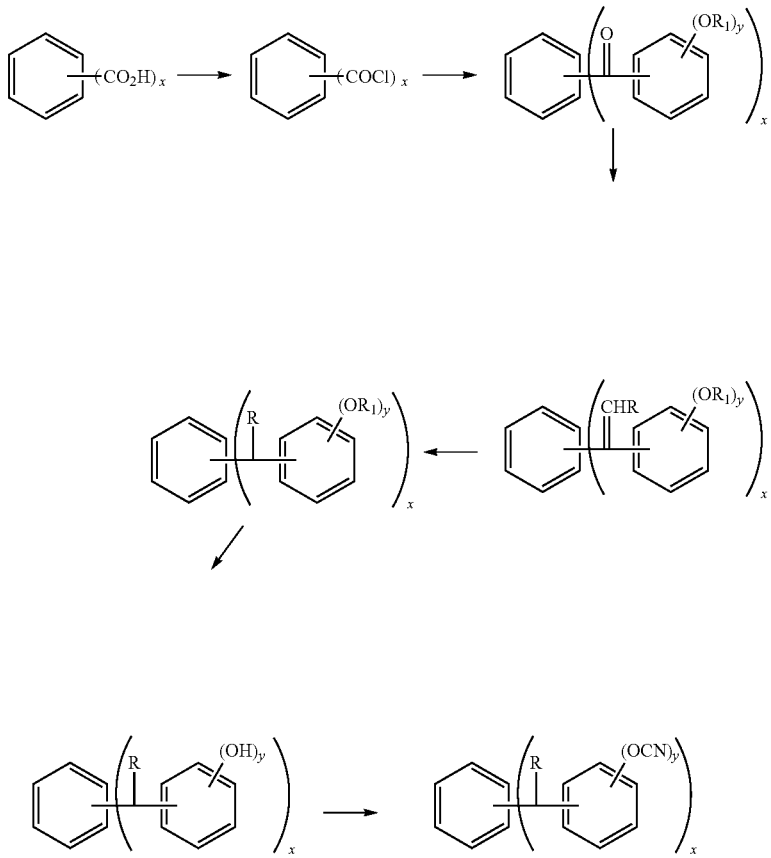

Some uses for embodiments of the invention include use in preparation of polymers with high thermal stability and mechanical strength. Such polymers may be utilized in jet aircraft and weapons systems.

The following examples are for illustration purposes only and not to be used to limit any of the embodiments.

Scheme 1. Example Synthesis of one particular monomer from the general Markush structure

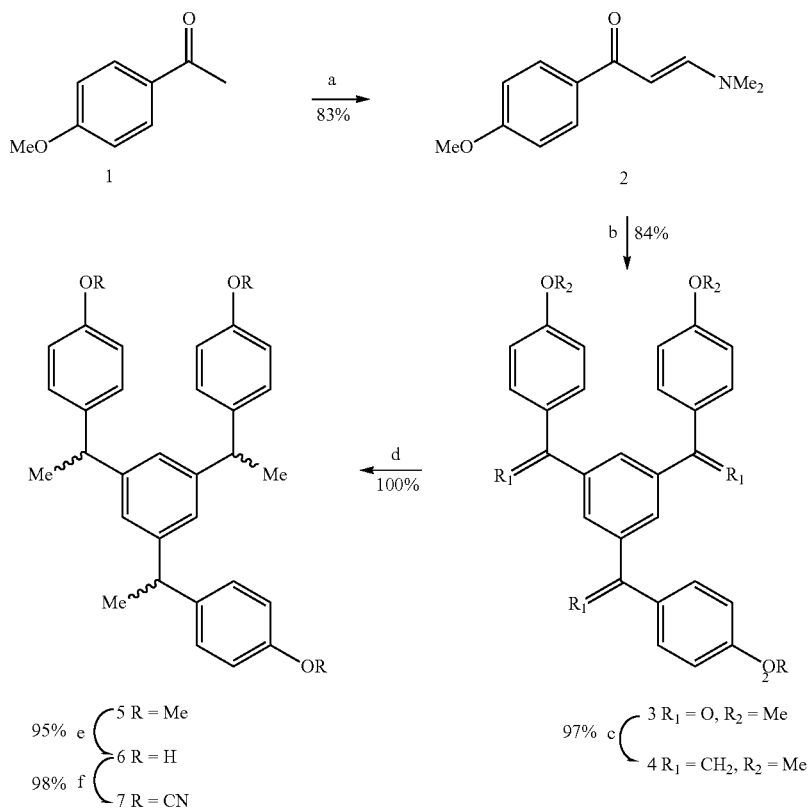

Reagents & conditions: a) Me$_2$NCH(OMe)$_2$, reflux; b) HOAc, pyridine, 120° C.; c) MeP(Ph)$_3$Br, KOtBu, THF; d) H$_2$, 5% Pd/C, EtOH, THF: e) pyridine HCl, 180° C.; f) BrCN, TEA, CHCl$_3$.

3-(Dimethylamino)-4'-methoxyacrylophenone (2)

In Scheme 1, A 2 L round-bottomed flask equipped with magnetic stirbar and reflux condenser was charged with 4-methoxyacetophenone (300.4 g, 2 mol) and N,N-dimethylformamide dimethyl acetal (358 g, 3 mol, 1.5 equiv) and the mixture was refluxed. The reaction progress was followed by $^1$H NMR analysis and was complete after 48 h reflux. Shortly after cooling to rt—(room temperature) the reaction mixture solidified. Filtration on a medium porosity glass frit gave a first crop of product (160.22 g) as yellow microcrystals after washing with Et$_2$O. The filtrate was rotary evaporated leaving a second crop of product (181.3 g). The title compound was obtained as light yellow plates from toluene. Yield: 341.5 g (83%). Mp: 82-85° C. (lit.[13] 90° C.). $^1$H NMR (300 MHz, CDCl$_3$, δ, ppm): 7.91 (d, J=8.8 Hz, 2H), 7.76 (d, J=12.5 Hz, 1H), 6.90 (d, J=8.8 Hz, 2H), 5.69 (d, J=12.4 Hz, 1H), 3.81 (s, 3H), 2.96 (bs, 6H). $^{13}$C NMR (75 MHz, CDCl$_3$, δ, ppm): 187.15, 161.86, 153.66, 133.07, 129.31, 113.21, 91.59, 55.21. Anal. calcd for C$_{12}$H$_{15}$NO$_2$: C, 70.22; H, 7.37; N, 6.82. Found: C, 70.38; H, 7.33; N, 6.79.

1,3,5-Tris(4-methoxybenzoyl)benzene (3)

A 2 L round-bottomed flask equipped with magnetic stirbar and reflux condenser was charged with glacial HOAc (683 mL, 11.4 mol) followed by pyridine (171 mL, 2.16 mol) and then 3-(dimethylamino)-4'-methoxyacrylophenone (2) (341.5 g, 1.66 mol) was added. The mixture was refluxed for 12 h. The mixture was allowed to cool to rt whereby copious solids precipitated. An addition funnel was equipped and H$_2$O (300 mL) was added dropwise with vigorous stirring. The mixture was filtered on a medium porosity glass frit to obtain a light tan, granular solid that was recrystallized from toluene. Yield: 223.3 g (84%). Mp: 179-183° C. (lit.[14] 175-176° C.). $^1$H NMR (300 MHz, DMSO-d$_6$, δ, ppm): 8.14 (s, 3H), 7.83 (d, J=8.8 Hz, 6H), 7.08 (d, J=8.8 Hz, 6H), 3.84 (s, 9H). $^{13}$C NMR (75 MHz, DMSO-d$_6$, δ, ppm): 192.97, 163.43, 138.03, 132.89, 132.44, 128.73, 114.10, 55.63. Anal. calcd for C$_{30}$H$_{24}$O$_6$: C, 74.99; H, 5.03. Found: C, 75.03; H, 4.80.

1,3,5-Tris(1-(4-methoxyphenyl)vinyl)benzene (4)

A 250 mL round-bottomed flask equipped with magnetic stirring bar and reflux condenser was charged with methyltriphenylphosphonium bromide (43.48 g, 122 mmol, 3.5 equiv), KOtBu (13.7 g, 122 mmol, 3.5 equiv) and THF (300 mL). After 1 h, 1,3,5-tris(4-methoxybenzoyl)benzene (3) (16.73 g, 34.8 mmol) was added portionwise over 30 min. After the addition, the mixture was refluxed for 1 h. Upon cooling to rt, H$_2$O (50 mL) was added and the mixture was neutralized by adding HOAc (1 g, 17 mmol, 0.5 equiv). The organic layer was separated and washed with brine (50 mL). The organic layer was dried over anhydrous $MgSO_4$ and rotary evaporated to a thick oil which slowly crystallized. The crude was dissolved in hot iPrOH (200 mL) and allowed to cool, whereby the title compound crystallized. Filtration on a medium porosity glass frit gave the title compound as white needles. Yield: 13.29 g (97%). Mp: 116-118° C. $^1$H NMR (300 MHz, $CDCl_3$, δ, ppm): 7.30 (d, J=8.8 Hz, 6H), 7.28 (s, 3H), 6.85 (d, J=9 Hz, 6H), 5.36 (d, J=1.0 Hz, 3H), 5.33 (d, J=1.0 Hz, 3H), 3.82 (s, 9H). $^{13}$C NMR (75 MHz, $CDCl_3$, δ, ppm): 159.56, 149.43, 141.77, 133.88, 129.48, 128.08, 113.78, 113.33, 55.49. Anal. Calcd for $C_{33}H_{30}O_3$: C, 83.51; H, 6.37. Found: C, 83.31; H, 6.35.

Racemic
1,3,5-Tris(1-(4-methoxyphenyl)ethyl)benzene (5)

A mixture of 1,3,5-tris(1-(4-methoxyphenyl)vinyl)benzene (4) (19.61 g, 41 mmol), 5% Pd/C (500 mg), THF (50 mL) and EtOH (50 mL) was hydrogenated (50 torr) on a Parr® apparatus for 5 h. After this time the uptake of hydrogen ceased. The mixture was filtered through diatomaceous earth to remove the catalyst and rotary evaporated leaving the title compound as a colorless, viscous oil. Yield: 19.6 g (100%). $^1$H NMR (300 MHz, $CDCl_3$, δ, ppm): 7.06 (d, J=8.7 Hz, 6H), 6.88-6.84 (m, 3H), 6.79 (d, J=8.9 Hz, 6H), 4.0 (q, J=7.5 Hz, 3H), 3.78 (s, 9H), 1.52 (d, J=7.3 Hz, 9H). $^{13}$C NMR (75 MHz, $CDCl_3$, δ, ppm): 157.16, 145.83, 145.78, 145.74, 138.03, 137.99, 137.97, 127.55, 123.54, 123.46, 123.41, 113.36, 54.61, 42.94, 42.92, 21.29. Anal. calcd for $C_{33}H_{36}O_3$: C, 82.46; H, 7.55. Found: C, 82.23; H, 7.40.

Racemic
1,3,5-Tris(1-(4-hydroxyphenyl)ethyl)benzene (6)

A 250 mL round-bottomed flask equipped with magnetic stirring bar was charged with racemic 1,3,5-tris(1-(4-methoxyphenyl)ethyl)benzene (5) (19.6 g, 41 mmol) and pyridine hydrochloride (56.8 g, 0.49 mol, 12 equiv). The mixture was protected with an $N_2$ bubbler and heated in a 180° C. oil bath for 5 h. The mixture was allowed to cool briefly to ~120° C. and then 55° C. $H_2O$ (100 mL) was added slowly to the mixture with vigorous stirring. The mixture was extracted three times with EtOAc (100 mL portions). The collected organic phase was washed with brine (200 mL) and dried over anhydrous $MgSO_4$. Rotary evaporation gave a thick, colorless oil that foamed under vacuum. Yield: 17.17 g (95%). $^1$H NMR (300 MHz, DMSO-$d_6$, δ, ppm): 9.12 (s, 3OH), 6.98 (d, J=8.6 Hz, 6H), 6.90 (s, 3H), 6.63 (d, J=8.6 Hz, 6H), 3.92 (q, J=7.2 Hz, 3H), 1.44 (d, J=7.5 Hz, 9H). $^{13}$C NMR (75 MHz, DMSO-$d_6$, δ, ppm): 155.35, 146.59, 146.53, 146.48, 136.69, 136.67, 136.65, 128.04, 123.88, 123.65, 114.96, 43.49, 43.46, 22.09, 22.04. Anal. calcd for $C_{30}H_{30}O_3 \cdot 0.65H_2O$: C, 80.02; H, 7.01. Found: C, 80.38; H, 7.41.

Racemic
1,3,5-Tris(1-(4-cyanatophenyl)ethyl)benzene (7)

A 250 mL round-bottomed flask equipped with magnetic stirring bar was charged with racemic 1,3,5-tris(1-(4-hydroxyphenyl)ethyl)benzene (6) (4.36 g, 99 mmol), cyanogen bromide (3.68 g, 34.7 mmol, 3.5 equiv) and anhydrous acetone (50 mL). The mixture was cooled in a −20° C. bath before dropwise addition of TEA (2.99 g, 297 mmol, 3 equiv). Near the end of the addition, copious solids (TEA·HBr) precipitated. After 1 h, ice cold $H_2O$ (100 mL) and $CH_2Cl_2$ (100 mL) were added and the phases were separated. The organic layer was washed with cold saturated $NaHCO_3$ (50 mL) and then brine (50 mL). After drying over anhydrous $MgSO_4$, the solvent was evaporated leaving a viscous, pale yellow oil. The crude product was dissolved in $CH_2Cl_2$ and filtered through a pad of silica gel and rotary evaporated to give the title compound in analytically pure form as a thick, colorless oil. Yield: 5.0 g (98%). $^1$H NMR (300 MHz, $CDCl_3$, δ, ppm): 7.21 (s, 12H), 6.84-6.81 (m, 3H), 4.09 (q, J=7.2 Hz, 3H), 1.57 (d, J=7.2 Hz, 9H). $^{13}$C NMR (75 MHz, $CDCl_3$, δ, ppm): 151.44, 146.23, 146.19, 146.15, 145.45, 145.42, 145.39, 129.66, 125.13, 125.08, 115.47, 109.14, 44.29, 22.16. FTIR (KBr, $cm^{-1}$): 2263 (OCN), 2233 (OCN). Anal. calcd for $C_{33}H_{27}N_3O_3$: C, 77.17; H, 5.30; N, 8.18. Found: C, 77.17; H, 5.32; N, 8.33.

Results of Synthesis

Where a range of values is provided, it is understood that each intervening value, to the tenth of the unit of the lower limit unless the context clearly dictates otherwise, between the upper and lower limits of that range is also specifically disclosed. Each smaller range between any stated value or intervening value in a stated range and any other stated or intervening value in that stated range is encompassed within the invention. The upper and lower limits of these smaller ranges may independently be included or excluded in the range, and each range where either, neither or both limits are included in the smaller ranges is also encompassed within the invention, subject to any specifically excluded limit in the stated range. Where the stated range includes one or both of the limits, ranges excluding either or both of those included limits are also included in the invention.

While the invention has been described, disclosed, illustrated and shown in various terms of certain embodiments or modifications which it has presumed in practice, the scope of the invention is not intended to be, nor should it be deemed to be, limited thereby and such other modifications or embodiments as may be suggested by the teachings herein are particularly reserved especially as they fall within the breadth and scope of the claims here appended.

What is claimed is:
1. A method for making cyanate esters, comprising:
combining benzenecarboxylic acid having one to six carbons (x) with at least one effective reagent to chlorinate said benzenecarboxylic acid to produce a one to six carbons (x=2 or 3) benzenecarbonyl chloride;

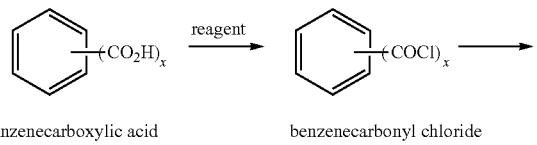

benzenecarboxylic acid      benzenecarbonyl chloride combining said benzenecarbonyl chloride with at least one alkoxybenzene compound under reaction by Friedel-Crafts conditions to produce a poly(alkoxybenzoyl)benzene having one to six carbons (x=2 or 3), (y=1-5);

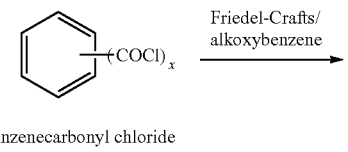

benzenecarbonyl chloride

-continued

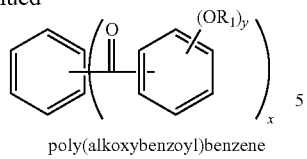
poly(alkoxybenzoyl)benzene combining said poly(alkoxybenzoyl)benzene with Wittig reagent to produce a poly(alkoxyphenylvinyl)benzene compound;

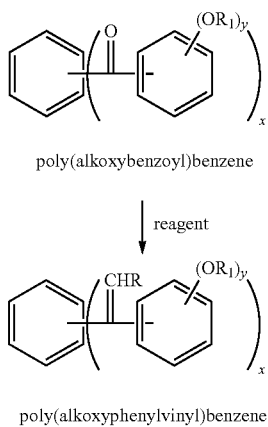

reducing of said poly(alkoxyphenylvinyl)benzene compound with at least one reducing agent to produce a poly(alkoxyphenylalkyl)benzene;

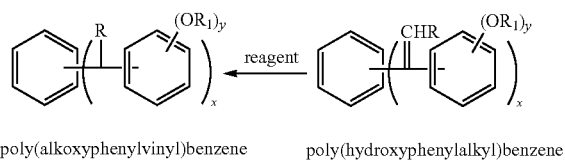

poly(alkoxyphenylvinyl)benzene     poly(hydroxyphenylalkyl)benzene combining said poly(alkoxyphenylalkyl)benzene with at least one demethylating reagent to produce poly(hydroxyphenylalkyl)benzene; and

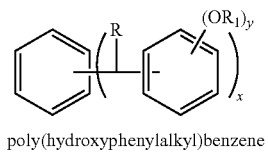
poly(hydroxyphenylalkyl)benzene cyanogen halide (CNBr or CNCl) and base

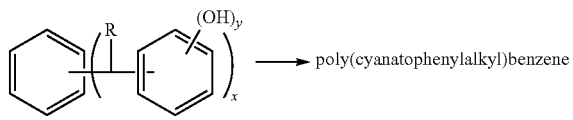

combining said poly(hydroxyphenylalkyl)benzene compound is cyanated by reaction with cyanogen halide (CNBr or CNCl) and base to produce a poly(cyanatophenylalkyl)benzene.

2. The method according to claim 1, wherein said reducing agent utilized to produce a poly(alkoxyphenylalkyl)benzene is selected from the group consisting of hydrogen, palladium on carbon, and Raney nickel.

3. The method according to claim 1, wherein said cyanogen halide comprises CNBr, CNCl, and any combination thereof.

4. The method according to claim 1, wherein said demethylating reagent comprises at least one of boron tribromide, pyridine hydrochloride, and aluminum triiodide.

5. The method according to claim 1, wherein said effective reagent comprises at least one of thionyl chloride.

* * * * *